US008029278B1

(12) United States Patent
Levine

(10) Patent No.: US 8,029,278 B1
(45) Date of Patent: Oct. 4, 2011

(54) INTRA-ORAL WHITENING DEVICE

(76) Inventor: Jonathan B. Levine, Purchase, NY (US)

( * ) Notice: Subject to any disclaimer, the term of this patent is extended or adjusted under 35 U.S.C. 154(b) by 447 days.

(21) Appl. No.: 12/186,641

(22) Filed: Aug. 6, 2008

(51) Int. Cl.
*A61C 3/00* (2006.01)
*A61C 5/00* (2006.01)
(52) U.S. Cl. .......................................... 433/29; 433/215
(58) Field of Classification Search ................... 433/29, 433/215
See application file for complete search history.

(56) References Cited

U.S. PATENT DOCUMENTS

| | | | |
|---|---|---|---|
| 5,702,250 A * | 12/1997 | Kipke | 433/37 |
| 6,155,832 A | 12/2000 | Wiesel | |
| 6,162,055 A | 12/2000 | Montgomery et al. | |
| 6,616,451 B1 | 9/2003 | Rizolu et al. | |
| 6,733,290 B2 * | 5/2004 | West et al. | 433/29 |
| 6,752,627 B2 | 6/2004 | Lin | |
| 6,783,363 B2 | 8/2004 | Eguchi et al. | |
| 6,902,397 B2 | 6/2005 | Farrell et al. | |
| 7,004,756 B2 | 2/2006 | Andersen | |
| 7,086,862 B2 | 8/2006 | Craig | |
| 7,144,249 B2 | 12/2006 | Rizoin et al. | |
| 7,160,111 B2 | 1/2007 | Baughman | |
| 7,223,270 B2 | 5/2007 | Altshuler et al. | |
| 7,250,155 B2 | 7/2007 | Yamaguchi et al. | |
| 2004/0193236 A1 | 9/2004 | Altshuler et al. | |
| 2005/0053898 A1 | 3/2005 | Ghosh et al. | |
| 2005/0064370 A1 | 3/2005 | Duret | |
| 2005/0074717 A1 * | 4/2005 | Cleary et al. | 433/24 |
| 2005/0158687 A1 * | 7/2005 | Dahm | 433/29 |
| 2005/0172429 A1 | 8/2005 | Russell et al. | |
| 2005/0202363 A1 * | 9/2005 | Osterwalder | 433/29 |
| 2005/0231983 A1 * | 10/2005 | Dahm | 362/800 |
| 2006/0019214 A1 * | 1/2006 | Lawrence et al. | 433/29 |
| 2006/0141422 A1 | 6/2006 | Philp, Jr. et al. | |
| 2006/0194164 A1 | 8/2006 | Altshuler et al. | |
| 2006/0257822 A1 | 11/2006 | Ghosh et al. | |
| 2007/0003905 A1 * | 1/2007 | Nguyen et al. | 433/215 |
| 2007/0015112 A1 | 1/2007 | Hochman et al. | |
| 2007/0020584 A1 | 1/2007 | Madray | |

FOREIGN PATENT DOCUMENTS

CA 2319890 3/2001

OTHER PUBLICATIONS http://www.exit15.com/briteteeth-laser-light-home-teeth-whitening "Sunshine Smiles Brite-Teeth Laser Light Home Teeth Whitening" p. 760 Nov. 15, 2007.
http://www.perfectlywhite.com/ "Welcome to Perfectly White.com (online since 2004)".
Smile Teeth Whitening Systems, 2005-2006 http://www.smileteeethwhitening.com/asupplies.html.

* cited by examiner

*Primary Examiner* — John J Wilson
(74) *Attorney, Agent, or Firm* — Michael A. Adler; Davidoff, Malito & Hutcher

(57) ABSTRACT

An intra-oral whitening device that has a mouthpiece in which is embedded a flexible circuit board and arrays of spaced apart lamps. The mouthpiece has a curvature. The lamps may be light emitting diodes that generate electromagnetic radiation, preferably in the white and blue light spectrum and the infrared and ultraviolet light spectrum. The arrays are positioned to expose the facial and lingual sides of the teeth for whitening when the mouthpiece is positioned to fit upper and lower rows of teeth to be whitened within accommodating recesses. The flexible circuit board is flexed to exhibit a curvature that follows a curvature of the mouthpiece.

21 Claims, 7 Drawing Sheets

INTRA-ORAL WHITENING DEVICE

BACKGROUND OF THE INVENTION

1. Field of the Invention

The present invention relates to a mouthpiece containing lamps to expose electromagnetic radiation to effect an oral treatment. For instance, the exposure could be to an adhesive whitening gel to whiten teeth. Alternatively, it may be to kill harmful bacteria in the mouth by exposure to the electromagnetic radiation.

2. Description of Related Art

Tooth whitening in the dental office takes up to 2 hours, expensive, is painful and the results will start to regress as early as 7 days after the treatment. The over-the-counter products are messy, can burn the fingers and the results usually take 7-10 days to see minimal improvement. The consumer needs a customizable whitening approach that gives the same results from professional whitening but at the convenience of the home and with much less money.

Whitening is governed by the concentration of the whitening active and the contact time (i.e., the time the agent is on the teeth). Whitening results are best achieved when there is high frequency of the whitening agent in a safe way and without the need of high concentration whitening agents that can burn the tissue. By increasing the frequency of the whitening by giving the consumer the ability to whiten at home, the regression phenomenon seen with the professional whitening will be eliminated.

It is desired to provide a whitening device that is coupled with a delivery system of the whitening gel and an adhesive that keeps hydrogen peroxide targeted to the area to whiten. Such a whitening device preferably causes no harmful breakdown by-products, and is delivered in a single dose hygienic way.

In addition, harmful bacteria is responsible for causing gum disease in the mouth. Specifically, the gram negative anaerobic bacteria is responsible. However, such bacteria is killed off from ultraviolet light exposure. It would therefore be desirable for a consumer to expose such bacteria to ultraviolet light on their own without relying on the assistance of professional help to do so.

SUMMARY OF THE INVENTION

One aspect of the invention resides in an intra-oral whitening device or mouthpiece suited to create a whitening and heat effect to increase a reaction rate of a photosensitive agent, i.e. hydrogen peroxide gel. The person whose teeth are to be whitened can wear the device and whiten his/hers teeth without the need of a professional office and is safe, effective and convenient.

In the past, the best whitening results have been done in the professional office that is expensive and time consuming. The intra oral whitening device of the present invention may allow consumers to whiten their teeth in the convenience of their home, to customize the whitening procedure for their own needs and to do so safely and effectively without the need for a dentist.

It is a further aspect of the invention to expose harmful bacteria in the mouth to electromagnetic radiation, such as ultraviolet light, to kill same in an effort to halt gum disease caused by such bacteria, e.g., the gram negative anaerobic bacteria.

BRIEF DESCRIPTION OF THE DRAWING

For a better understanding of the present invention, reference is made to the following description and accompanying drawings, while the scope of the invention is set forth in the appended claims:

DETAILED DESCRIPTION OF THE INVENTION

Figure 1:
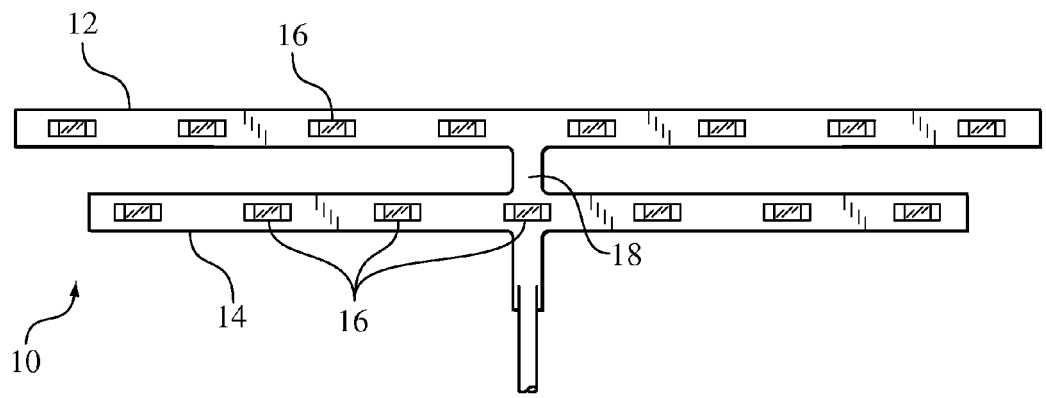
FIG. 1 is a plan view of a flexible circuit board extending in a plane in accordance with the invention.

Turning to the drawing, FIG. 1 shows a flexible circuit board 10 with dual parallel arrays 12, 14 of ultraviolet light emitting diode (UV LED) lamps 16 in accordance with the invention. The circuit board 10 has a central connecting strip 18 that extends between the dual parallel arrays 12, 14 at a generally central location. The flexible circuit board 10 is flexed to form a curvature as part of an intra-oral whitening device 20 of FIG. 3.

Figure 2:
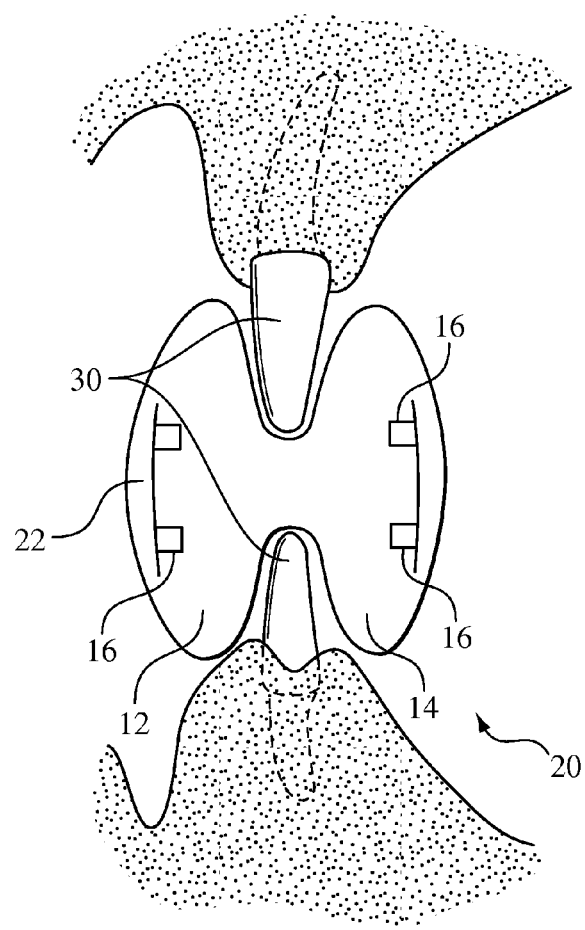
FIG. 2 is a cross-section of a mouthpiece in accordance with the invention in position to whiten teeth through exposure to electromagnetic radiation emitted from lamps that are embedded in the mouthpiece.
Figure 3:
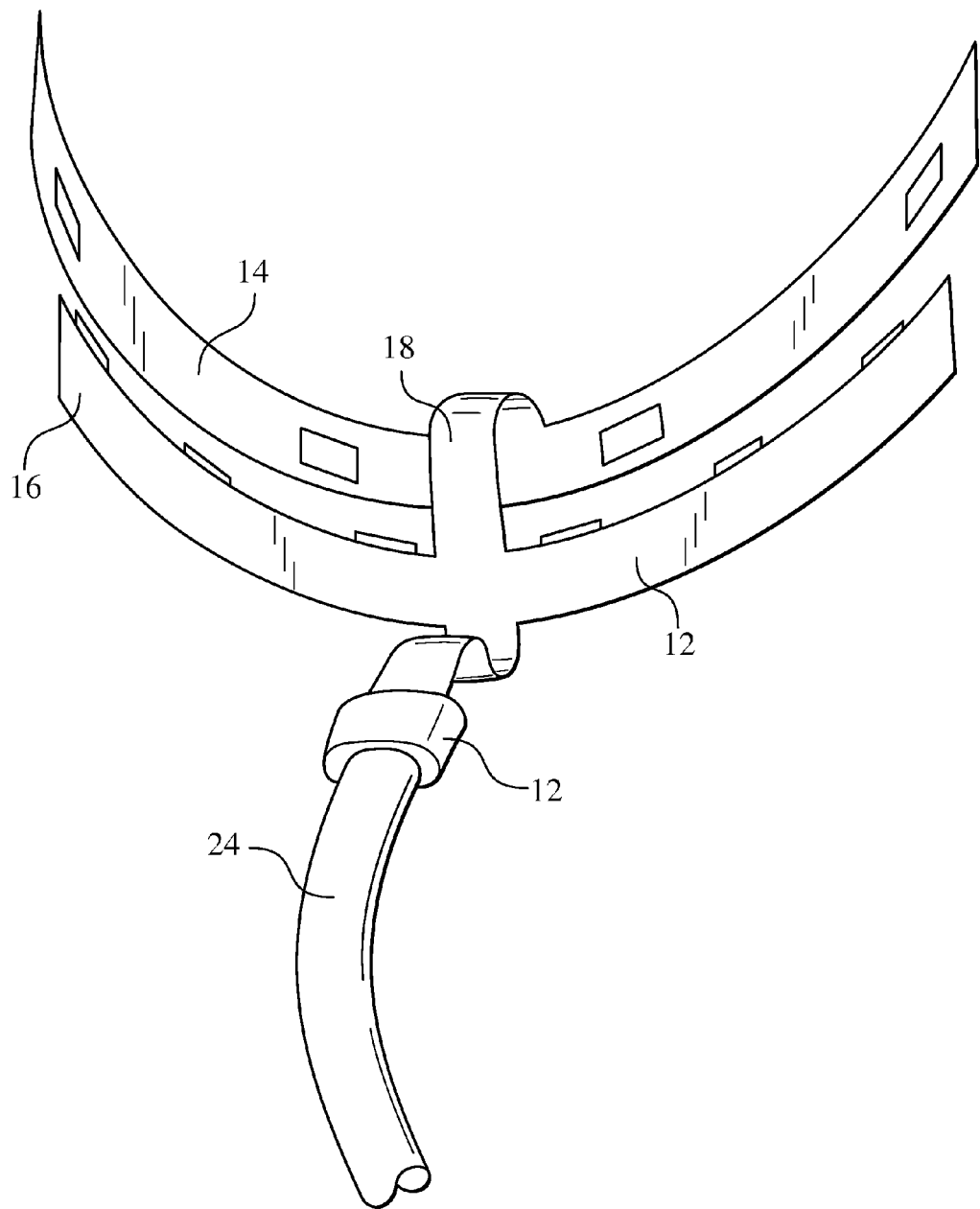
FIG. 3 is an isometric view of the flexible circuit board in a flexed, curved configuration in accordance with the invention and also showing the location of lamps, power cord and socket and plug connection.

Starting from the planar orientation of the flexible circuit board 10 shown in FIG. 1, the circuit board 10 is folded or flexed at a the central connecting strip 18 so that the respective arrays 12, 14 of lamps 16 are opposed to each other in the manner shown in FIGS. 2 and 3. The circuit board 10 is then curved in the manner shown in FIG. 3. These two steps help in the positioning of the LED lamps 16 on both the facial and lingual sides of the teeth to be treated, as shown in FIG. 2. That is, such position is realized upon positioning part of the assembly, i.e. a mouthpiece 22 containing the arrays 12, 14 of lamps 16, within the mouth of a person whose teeth are to be whitened.

The intra-oral whitening device 20 of FIGS. 2 and 3 is made of moldable, flexible, plastic that exposes both arches upper and lower to the EM radiation in the 300-990 nm range and heat less than 52 degrees centigrade. The combination of the plastic device, light and heat, adhesive whitening gel all together will create effective whitening that takes much less time than conventional whitening techniques and is safe and effective.

The lamps 16 serve as light sources and are preferably LED lamps with a high concentration in the white and blue and the non-visible light spectrum (infrared and UV), which is known to form highly effective bleaching ions when exposed to the unseen portion of the spectrum. The light sources are embedded into a moldable, flexible plastic mouthpiece 22 on grids that surround the upper and lower front surfaces of the teeth with the necessary light along with heat that has two or three levels stopping at 52 degree Centigrade to avoid pulpal sensitivity. The plastic mouthpiece 22 is preferably made from a transparent or translucent material.

Figure 4:
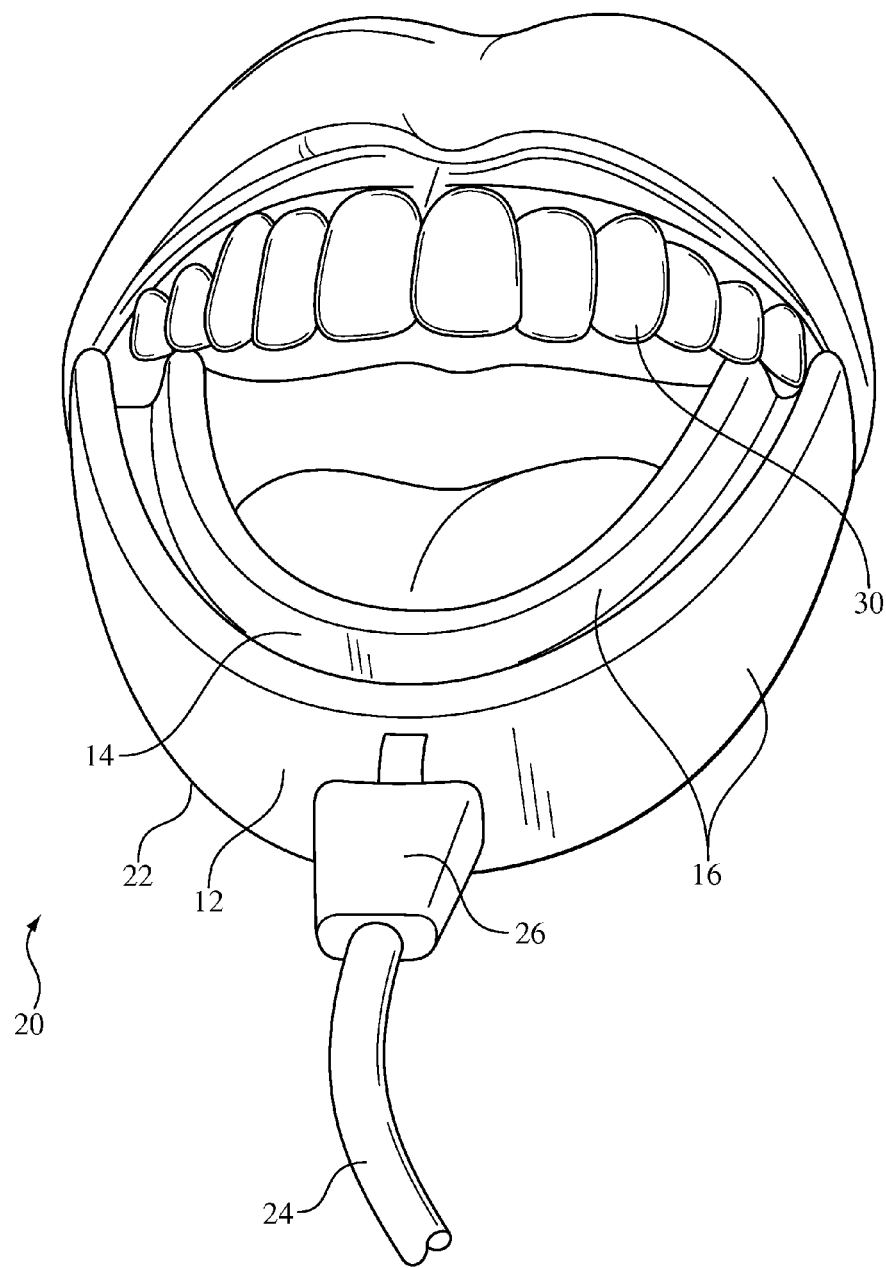
FIG. 4 is an isometric view of the mouthpiece being positioned in a person's mouth. The mouthpiece embeds the curved flexible circuit board of FIG. 3 as well as the lamps. The power cord and the socket and plug connection is also depicted.

The lamps 16 may be positioned along a full length of the flexible circuit board, inclusive of the curvature of the flexed circuit board 10 at the base of the U-shape it has within confines of the mouthpiece 22 (see FIGS. 3 and 4). The curvature of the flexible circuit board 10 generally follows the curvature of the mouthpiece 22.

Turning to FIG. 2, the LED lamps 16 shine on both upper and lower teeth 30 substantially equally as the patient (whose mouth contains the mouthpiece 22 of the intra-oral whitening device 20) closes down the mouth. The mouthpiece 22 has a generally H-shaped cross section with upper and lower recessed portions to respectively accommodate therein the upper and lower rows of teeth 30 to be treated (see FIG. 2). The recessed portions are defined between the sides of the H-shaped mouthpiece 22 with one 12 or 14 array of lamps 16 being arranged on each side of the H-shaped mouthpiece 22. As shown in FIG. 2, the lamps 16 are oriented to direct electromagnetic radiation toward one another so that when teeth 30 are situated in the recessed portions, the array 12 of lamps 16 emits electromagnetic radiation toward the facial side of the teeth 30 while the array 14 of lamps 16 emits electromagnetic radiation toward the lingual side of the teeth 30.

The power supply may be intra-oral or extra-oral and would be advantageous if the consumer can customize the whitening by dialing the level of heat and light, such as by choosing as many as two or three light and heat intensities. The power supply may use a power cord 24 to provide power via a plug and socket connection 26 with the flexible circuit board 10. An end of the cord 24 may have the plug and the circuit board 10 may have the socket or vice versa.

Turning to FIG. 3, the central positioning also inherently provides treatment of biting surfaces of teeth 30, such as for purposes of changing a condition of the biting surfaces for the better as a result of prolonged exposure to electromagnetic radiation from the lamps. The inherent light piping quality of the materials appropriate for use in the mouthpiece of the present invention enhances with lensing or reflective films.

A headset may be provided that uses the technology of T-ink, the use of printed technology that takes the circuit board and incorporates this into the printed design eliminating buttons, wires and switches.

The headset gives an interactive component to the user, explain the use of the device, offer important instructions and they can get key learnings from the doctor, and can set up a music timer to the headset.

As an alternative to the headset, and any handheld device may be used with appropriate control buttons and may be small enough to fit in a shirt pocket or held to one's blouse with a clip. This enables hands free operation while the lamps are operating.

FIGS. 5-8 illustrate three approaches intended to direct electromagnetic radiation such as light evenly across tooth faces. The light travels along a light path in which the light changes direction. After leaving the light emitting diode, the light strikes an angled mirror surface to be diverted toward reflective surfaces that in turn reflect the light toward the tooth faces. Such a light path is analogous to the path taken by light to travel through a periscope.

Figure 5:
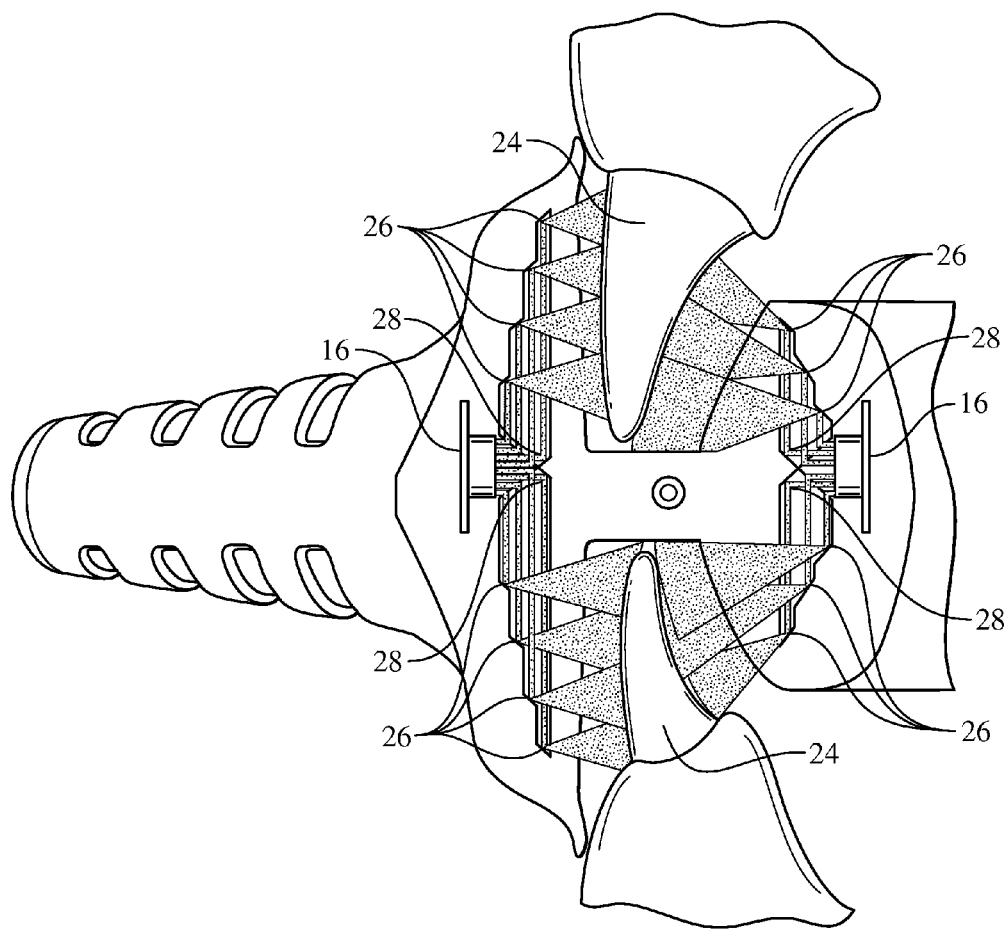
FIG. 5 is an isometric view of the flexible circuit board of the invention arranged in position on either side of incisor teeth.
Figure 6:
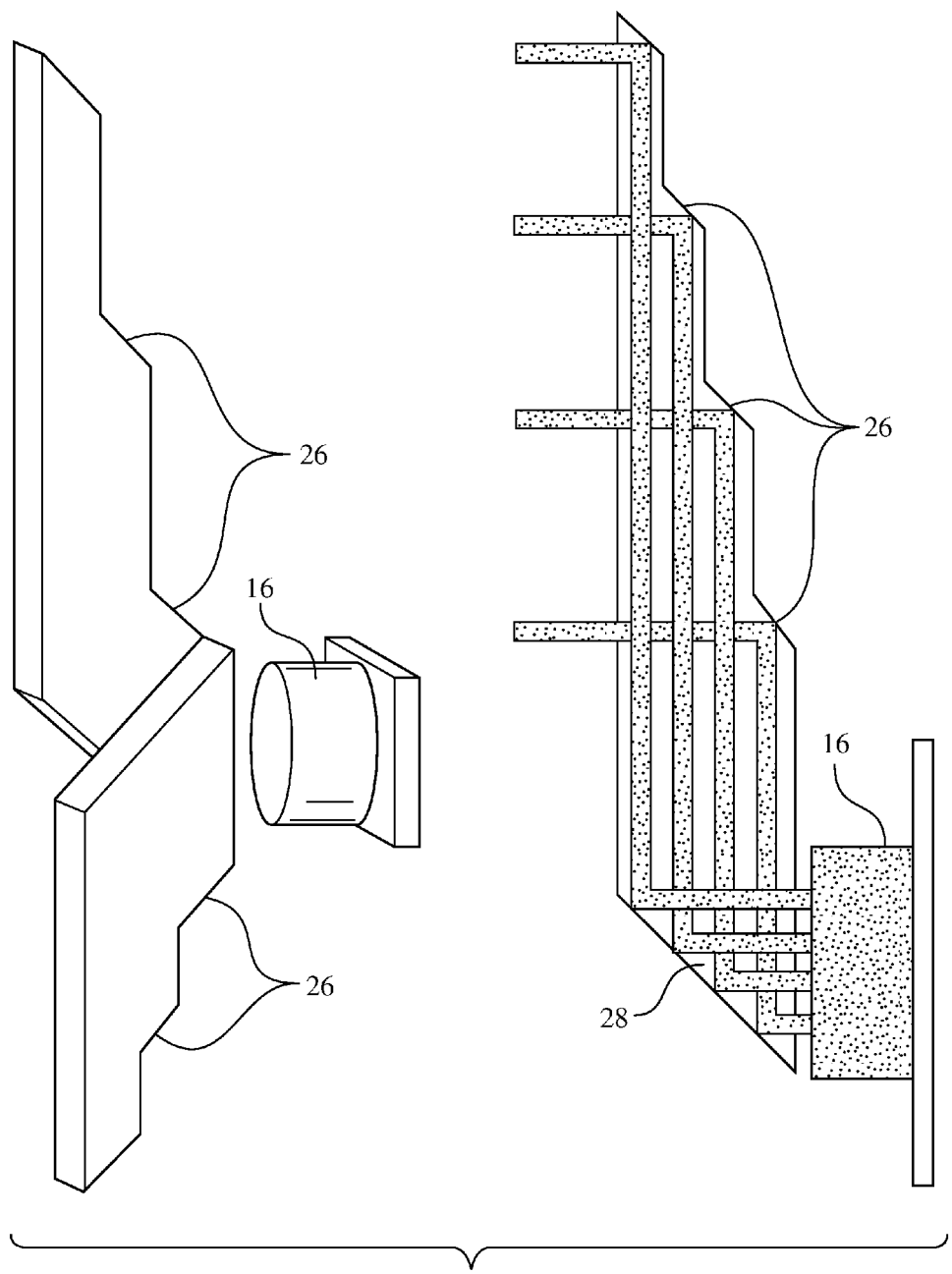
FIG. 6 is a schematic representation of a light emitting diode (LED), which is powered through the flexible circuit board of the invention, to direct light at a reflector, which reflects light emitted from the LED.

FIG. 5 shows "periscope" features molded as an over-molded insert to direct light to upper and lower incisor teeth. Staged or stepped, emitting reflectors 24 extend the area covered by reflecting light from light emitting diodes toward tooth surfaces. FIG. 6 shows an LED lamp 16 emitting its light at an angled mirror reflector 28, which reflects light toward the staged or stepped, emitting reflectors 24, which in turn reflects the light at tooth surfaces of incisors to be treated (e.g., whitened). The reflector 24 is angled to direct the reflected light away from the LED lamp 16.

Figure 7:
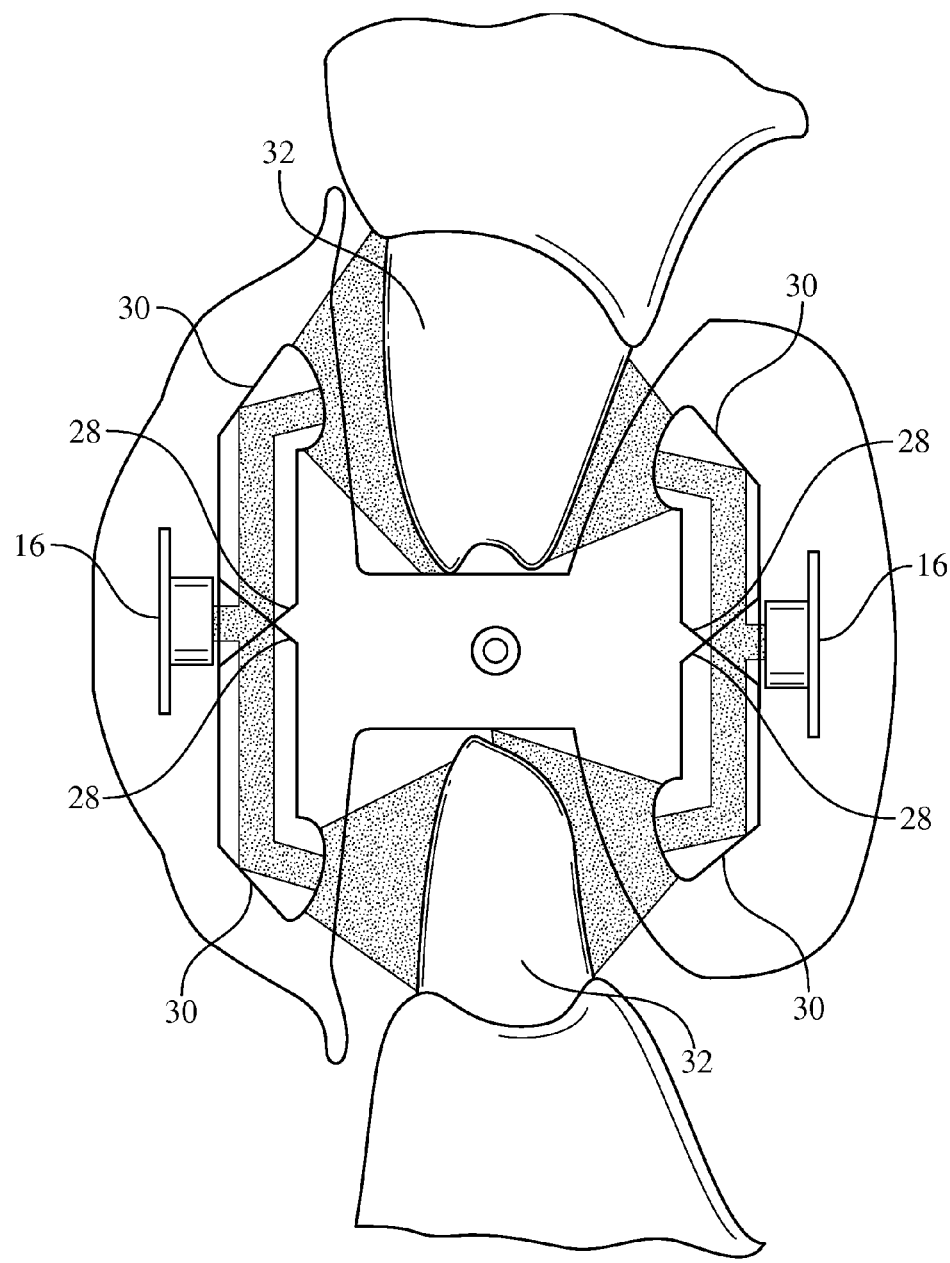
FIG. 7 is a plan view of the flexible circuit board of the invention in position on either side of canine/premolar teeth.

FIG. 7 shows another approach. "Periscope" features are molded as an over-molded insert. Distal lensing 30 extend the area covered by the light emission from LED lamps 16. Light emitted from the LED lamps 16 strike mirror reflectors 32, which reflect the light to the distal lensing 30, which in turn reflects the light toward surfaces of canine/premolar teeth.

Figure 8:
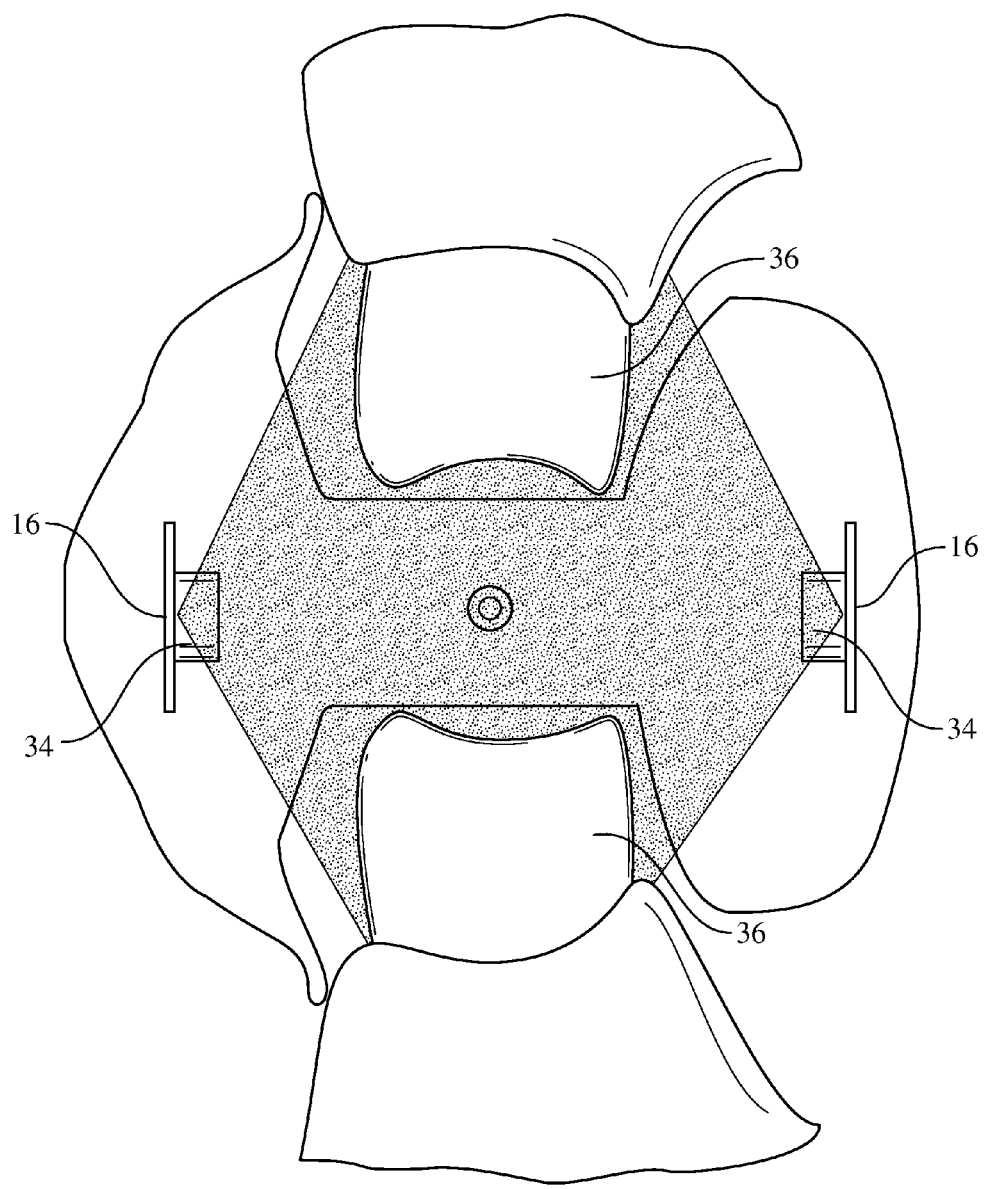
FIG. 8 is a plan view of the flexible circuit board of the invention in position on either side of molar teeth.

FIG. 8 shows yet another approach. A standard 120 degree emission LED lamps 16 are provided, with lensing 32 molded into the elastomer. Light from the LED lamps 16 is directed at the lensing 32, which directs the light at tooth surfaces of molars.

While the foregoing description and drawings represent the preferred embodiments of the present invention, it will be understood that various changes and modifications may be made without departing from the spirit and scope of the present invention.

What is claimed is:

1. An intra-oral device for effecting an oral treatment, comprising:
   a mouthpiece having a curvature, the mouthpiece having a cross-section indicative of a H shape so as to have first and second recessed portions that extend in opposite directions from each other, the first recessed portion being configured to accommodate at least part of an upper row of a person's teeth and the second recessed portion being configured to accommodate at least part of a lower row of the person's teeth simultaneously, the mouthpiece further having an inner portion adapted to be situated on a lingual side of teeth when situated in the first and second recessed portions, an outer portion adapted to be situated on a facial side of the teeth when situated in the first and second recessed portions, and a connecting portion that connects the inner and outer portions;
   a flexible circuit board within confines of the mouthpiece and likewise being curved to follow the curvature of the mouthpiece;
   a plurality of arrays of lamps electrically connected to the flexible circuit board, the lamps being spaced from each other within the arrays and the arrays being spaced from each other such that at least one array is arranged on a first side of the first and second recessed portions and at least one other array is arranged on a second side of the first and second recessed portions, the arrays extending alone a length of the mouthpiece alongside the first and second recessed portions, the lamps being configured to emit electromagnetic radiation during their operation, the lamps in the arrays of lamps on both the first and second sides of the first and second recessed portions being situated at least partly opposite the connecting portion; and
   light guiding structure arranged in the mouthpiece in a path of the electromagnetic radiation being emitted by each of the arrays of lamps to guide the electromagnetic radiation being emitted by each array of lamps into both the first and second recessed portions such that electromagnetic radiation from all of the lamps in the array of lamps on the first side of the first and second recessed portions is guided into both the first and second recessed portions from the first side thereof and electromagnetic radiation from all of the lamps in the array of lamps on the second side of the first and second recessed portions is guided into both the first and second recessed portions from the second side thereof, the light guiding structure being situated both above and below the arrays of lamps in both the inner and outer portions.

2. The device of claim 1, wherein the mouthpiece is formed of a plastic material having a transparent or translucent property, the lamps being embedded within the plastic material to emit electromagnetic radiation through the transparent or translucent material during operation of the lamps.

3. The device of claim 1, wherein the array of lamps on the first side of the first and second recessed portions is parallel and opposed to the array of lamps on the second side of the first and second recessed portions.

4. The device of claim 1, further comprising a power supply and a power cord, the power cord extending from the power supply to electrically connect with the flexible circuit hoard via a plug and socket connection at the mouthpiece.

5. The device of claim 4, wherein the curvature of the mouthpiece imparts a U-shape to the mouthpiece, the plug and socket connection is at a base of the U-shape of the mouthpiece.

6. The device of claim 1, wherein the lamps are light emitting diodes.

7. The device of claim 6, wherein the light emitting diodes have a concentration in a visible light spectrum, which is selected from a group consisting of white and blue and a combination thereof, and in a non-visible light spectrum, which is selected from a group consisting of infrared, ultraviolet and a combination thereof.

8. The device of claim 1, wherein the lamps are configured to provide electromagnetic radiation in a range of 300-990 nm and to give off heat in an amount that is less than 52 degrees Centigrade such that electromagnetic radiation and heat are simultaneously provided by the arrays of lamps on both the first and second sides of the first and second recessed portions.

9. The device of claim 1, further comprising an adhesive whitening gel positioned to be exposed to the electromagnetic radiation from at least some of the lamps.

10. A method of use of the device of claim 9, comprising whitening teeth situated in the first and second recessed portions as a consequence of exposing the adhesive whitening gel to electromagnetic radiation from the lamps.

11. The device of claim 1, wherein the light guiding structure comprises reflective films arranged to be exposed to the electromagnetic radiation from at least some of the lamps and to reflect same.

12. The device of claim 1, wherein the light guiding structure comprises lenses arranged to allow the electromagnetic radiation from at least some of the lamps to pass through and become focused by the lenses.

13. The device of claim 1, further comprising a user interface positioned to allow a user to select a plurality or light intensities that the lamps are to radiate during their operation and to adjust amounts of heat to be generated by the lamps during their operation.

14. The device of claim 13, wherein the user interface is spaced away from the mouthpiece.

15. The device of claim 13, further comprising a headset that incorporates the user interface.

16. The device of claim 1, wherein the light guiding structure comprises staged reflectors and angled reflectors, the angled reflectors being arranged in a path of electromagnetic radiation emission from the lamps to divert the electromagnetic radiation emission toward the staged reflectors, which in turn reflect the electromagnetic radiation emission.

17. The device of claim 1, wherein the light guiding structure comprises distal lensing and angled reflectors, the angled reflectors being arranged in a path of electromagnetic radiation emission from the lamps to divert the electromagnetic radiation emission toward the distal lensing, which in turn reflect the electromagnetic radiation emission.

18. The device of claim 1, wherein the lamps are encapsulated with an elastomer, and wherein the light guiding structure comprises lensing in the elastomer to angle emitted electromagnetic radiation from the lamps.

19. A method of use of the device of claim 1, comprising emitting ultraviolet light as the electromagnetic radiation from the lamps, and directing the ultraviolet light at harmful bacteria in the mouth to kill same.

20. A method of use of the device of claim 1, comprising exposing biting surfaces of teeth situated in the first and second recessed portions to the electromagnetic radiation from the lamps.

21. A method of use of the device of claim 1, wherein the light guiding structure comprises reflective surfaces, the method comprising diverting the emitted electromagnetic radiation from the lamp to strike the reflective surfaces that reflect the emitted electromagnetic radiation toward surfaces of teeth situated in the first and second recessed portions so that the emitted electromagnetic radiation changes direction while traveling through a path to reach the surfaces of the teeth situated in the first and second recessed portions.

* * * * *